United States Patent [19]
Lopez

[11] Patent Number: 6,013,821
[45] Date of Patent: Jan. 11, 2000

[54] REMOVAL OF SILYLATED COMPOUNDS FROM SOLVENT AND GAS WASTE STREAMS

[75] Inventor: Rafael Lopez, Gurnee, Ill.

[73] Assignee: Abbott Laboratories, Abbott Park, Ill.

[21] Appl. No.: 09/105,330

[22] Filed: Jun. 25, 1998

[51] Int. Cl.$^7$ ....................................................... C02F 2/08
[52] U.S. Cl. .......................... 556/428; 556/412; 556/466; 556/467
[58] Field of Search .................................... 556/428, 466, 556/412, 467

[56] References Cited

U.S. PATENT DOCUMENTS

| | | |
|---|---|---|
| 5,068,011 | 11/1991 | Lee et al. . |
| 5,443,697 | 8/1995 | Berg . |
| 5,493,042 | 2/1996 | Ault et al. ................................ 556/466 |

FOREIGN PATENT DOCUMENTS

| | | |
|---|---|---|
| 61-11203 | 5/1986 | Japan . |
| 63-20833 | 4/1988 | Japan . |

OTHER PUBLICATIONS

The Canadian Journal of Chemical Engineering, vol. 66, Oct., 1988; pp. 802–807, Al–Jarallah, et al. "Kinetics of Methyl Tertiary Butyl Ether Synthesis Catalyzed by Ion Exchange Resin".

*Primary Examiner*—Paul F. Shaver
*Attorney, Agent, or Firm*—Portia Chen

[57] ABSTRACT

The present invention provides a method of removing silylated compounds from a solvent or gas waste stream, comprising treating the waste stream with sulfuric acid to form a silylated sulfuric acid ester and separating the ester from the waste stream. The invention further provides for recovering a silylated compound from the separated ester.

12 Claims, 1 Drawing Sheet

REMOVAL OF SILYLATED COMPOUNDS FROM SOLVENT AND GAS WASTE STREAMS

TECHNICAL FIELD

The present invention relates to separation of silylated compounds from either a solvent or a gas waste stream. The silylated compounds can be recovered from the waste stream and purified for reuse.

BACKGROUND OF INVENTION

Pharmaceutical manufacturing processes produce medicinal compounds and products useful in treating a broad spectrum of health conditions and concerns. These processes often require large quantities of solvent or gas which result in the production of waste solvents, gases, and impurities. When possible, a waste stream is separated into its components, purified, and reused or recycled. Consequently, the separation and recovery of these manufacturing waste streams achieves cost savings in the industry as well as provides an ecological benefit to the environment.

Common pharmaceutical processes use silylation agents to react with active hydrogen present in molecules to form protector groups during the synthesis of compounds. Excess reagents and removed protecting groups are carried away in the solvent waste stream. When the reaction is carried out in solvents having a relative volatility near unity, i.e. the boiling point and volatility of the compounds are nearly the same, compounds become very difficult to separate and are often disposed off as waste.

Silylated compounds create complications in gas waste streams as well as solvent waste streams. During manufacturing processes, residual silylated compounds in a gas waste stream decompose to form silica which collects on equipment surfaces, creating a need for frequent maintenance and cleaning of the manufacturing equipment. Efficient in process methods of silica removal would reduce or eliminate downtime required for maintenance and cleaning of the manufacturing equipment.

Conventional methods of distillation have been unsuccessful at separating silylated compounds from solvent waste streams. Fractional distillation methods are generally known for separation of compounds having distinctly different boiling points and are not effective in separating components of an azeotropic composition. Other methods that have been described for separating silylated compounds require mixing a feed mixture with a separate reagent in a controlled reaction.

Recent methods of distilling a solvent mixture in the presence of a suitable reagent have been disclosed for separating solvent components having a relative volatility close to unity. These methods, known as reactive distillations, involve introducing an extractive agent into a distillation to affect the volatility of a feed component sufficiently to facilitate separation of the feed mixture.

U.S. Pat. No. 5,068,011 discloses an extractive distillation process for separating monoolefins from an alkane solvent with N-mercaptoalkyl-2-pyrrolidone.

Extractive distillation as described in U.S. Pat. No. 5,443,697 separates isomers of 1-heptene from heptane employing diacetone alcohol, ethylbutyrate and dimethylsulfoxide as the extractive agent.

Japanese Patent No. JP-112032 discloses a method of recovering 1,2-dichloroethane which is characterized by the fact that concentrated sulfuric acid is added to a mixed solution of 1,2-dichloroethane. The mixed solution is separated into two layers, rinsed, and dried over calcium chloride for dessication.

Consequently, there remains a need for convenient, effective methods of separation that provide for recovery of solvent and gas waste streams containing silylated compounds. One object of the invention is to provide a method of removing and optionally recovering silylated compounds from a solvent waste stream by a process of reactive distillation. Another object of the invention is to provide a method of recovering a purified solvent from the solvent waste stream. A further object of the invention is to provide a method of removing and optionally recovering silylated compounds from a gas waste stream. These and further objects of the invention will be apparent from the following description of the preferred embodiments thereof.

SUMMARY OF THE INVENTION

Figure 1:
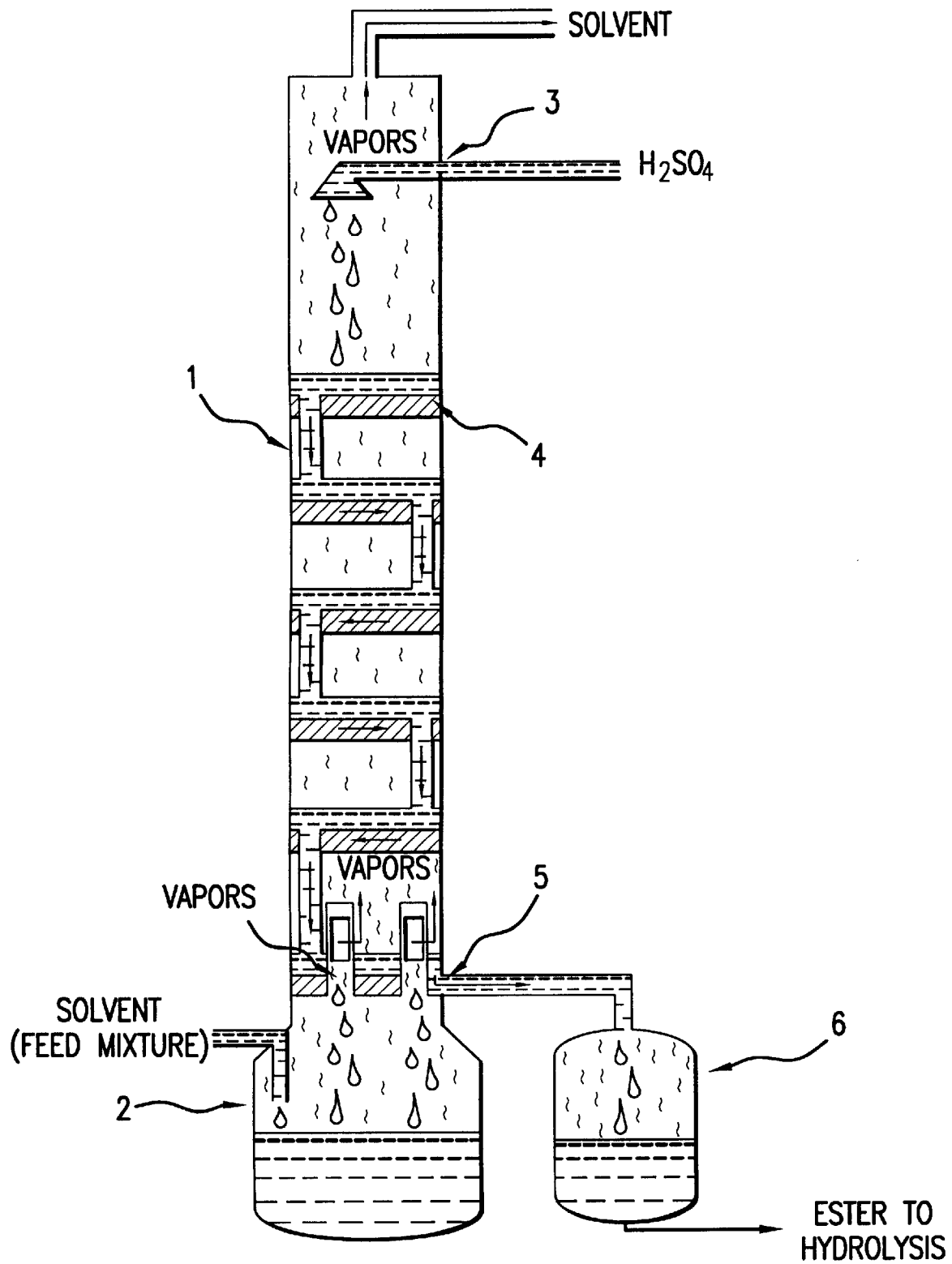
FIG. 1 illustrates a reactive distillation process in accordance with the invention.

The present invention relates to a novel method of removing silylated compounds from either a solvent or a gas waste stream. Removal of the silylated compounds from a solvent waste stream involves reactive distillation of the solvent waste stream with sulfuric acid. Removal of the silylated compounds from a gas waste stream involves treating a gas waste stream with sulfuric acid solution.

One aspect of the invention relates to a method of removing silylated compounds from a solvent waste stream comprising:

(a) reactively distilling a solvent waste stream with sulfuric acid to form a silylated sulfuric acid ester; and (b) separating the ester from the waste stream.

The silylated compounds can be recovered from the separated ester by hydrolyzing the recovered ester. In addition, the solvent waste stream can also be recovered, recycled, or reused as part of the same or a different manufacturing process.

Another aspect of the invention relates to a method of removing silylated compounds from a gas waste stream comprising:

(a) treating a gas waste stream with sulfuric acid to form a silylated sulfuric acid ester; and (b) separating the ester from the gas waste stream.

Silylated compounds are optionally recovered by treating the silylated sulfuric acid ester with hydrolysis. The gas waste stream is generally recirculated in the manufacturing process once the silylated compounds are removed.

Processes of the present invention provide efficient and improved methods for removing silylated compounds from both the solvent and gas waste streams. The recovered solvents, gases, and compounds can be used or recycled in useful pharmaceutical production processes. Removal and recovery processes of the invention provide improved economic and environmental advantage in pharmaceutical product manufacturing.

DETAILED DESCRIPTION OF THE INVENTION

The process of the present invention involves treating a solvent or a gas waste stream with sulfuric acid to form a silylated sulfuric acid ester which can be removed from the waste stream. In one aspect of the invention, reactive distillation of the solvent waste stream with sulfuric acid affords the silylated sulfuric acid ester, which is removed and optionally treated to recover a silylated compound. In this aspect of the invention, the solvent separated from the ester contains less than 100 ppm impurities and is suitable for recycling or reuse. In another aspect of the invention, silylated compounds are removed and optionally recovered from a gas waste stream via a sulfuric acid esterification process.

The process involves reactively distilling a solvent waste stream with concentrated sulfuric acid in a gas-liquid reactive distillation to remove silylated components in the waste stream. Methods of reactive distillation are well-known processes. A summary of the processes of reactive distillation is found in Al-Jarallah et al., *Canadian Journal of Chemical Engineering*, 66: 802–807 (1988), which is herein incorporated by reference. In a typical reactive distillation process, an extractive reagent reacts with components in a feed mixture to be separated and alters the relative volatility of the components to achieve an effective separation.

In this aspect, the invention relates to manipulating the known processes of reactive distillation to allow removal of silylated compounds from a solvent waste stream. A process according to the invention uses sulfuric acid solution as an extractive reagent to form a silylated sulfuric acid ester having a relative volatility greater than 1 when compared with the solvent. The reaction proceeds according to the following reaction equation:

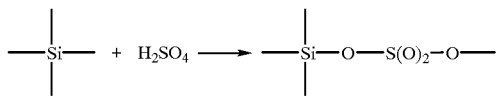

Suitable sulfuric acids are reagent grade sulfuric acid solutions suitable for distillations. Preferably, the sulfuric acid is at least 96% grade in purity.

Components of the feed mixture will vary depending on the waste stream to be treated. Common components of a solvent waste stream may include organic solvents, inorganic solvents, aqueous solvents, anhydrous solvents or any combination thereof. The solvent waste stream will generally include the silylated compound to be removed and at least one hydrocarbon component selected from the group consisting of alkanes, alkenes, substituted alkanes, substituted alkenes, and aromatic compounds.

Exemplary suitable alkanes present in the solvent waste stream will include, but are not limited to, methane, ethane, propane, n-butane, isobutane, n-pentane, hexane, heptane, octane, nonane, decane and the like, or mixtures thereof. Related alkenes, such as butene, pentene, hexene, heptene, octene, nonene, decene, and the like, and mixtures thereof, are also suitable components of the feed mixture.

Substituted alkane and substituted alkene compounds refers to alkyl, aryl and halosubstituted alkanes and alkenes, respectively. Exemplary alkyl-substituted hydrocarbons include, but are not limited to, 2-methylbutane, 2-methylpentane, 3-methylpentane, 2-methylhexane, 3-methylhexane, 2,2-dimethylpentane, 2,4-dimethylpentane, 3,3-dimethylpentane, 2,4-dimethylpentane, 2,2,3-trimethylbutane, 2-methylpropene, 2-methyl-1-butene, 2,3-dimethyl-1-butene, 2-methyl-1-hexene, 2-methyl-2-hexene, 3-methyl-2-hexene, 3-methyl-3-hexene, 2-methyl-1-heptene and the like, or a mixture thereof. Aromatic and aromatic-substituted hydrocarbon compounds used in may include for example, benzene, toluene, o-methyltoluene, p-methyltoluene, 1,2-dichlorobenzene, 1,3-dichlorobenzene, 1,4-dichlorobenzene, propane-benzene, propene-benzene, butane-benzene, butene-benzene, pentane-benzene, pentene-benzene, hexane-benzene, hexene-benzene, heptane-benzene, heptene-benzene, octane-benzene, octene-benzene, nonane-benzene, nonene-benzene, decane-benzene, decene-benzene and the like, or a mixture thereof. Halosubstituted compounds as referred to herein are bromine, chlorine, fluorine, and iodine substituted hydrocarbons, for example, bromoethane, 1,2-dibromoethane, chloroform, dichloromethane, 1,2-dichloroethane, fluoroethane, 1,2-difluoroethane, iodoethane, 1,2-diiodoethane, and the like or a mixture thereof. One or more of any number of isomers for any particular solvent can treated in a process of the invention, for example: 1-butene, 2-butene, 1-pentene, 2-pentene, 1-hexene, 2-hexene, 3-hexene, 1-heptene, 2-heptene, 3-heptene, and the like.

Typically, a solvent waste stream treated in the invention will comprise heptane and any isomers thereof.

Other additional components comprise common solvents, including but not limited to water, acetonitrile, isopropyl alcohol, toluene, benzene, and the like or a mixture thereof, and the silylated compounds to be removed. The suitable feed mixture will have a boiling point higher than the compounds being separated from the feed mixture.

Common silicon containing compounds present in the solvent waste stream comprise silicon, silanes, siloxanes, silicon halides, silicon oxides, silyl halides, and the like. Typical silylated compounds present in the solvent waste stream comprise hexamethyldisilazane, hexamethyldisiloxane, trimethylsilane, tetramethylsilane, trimethylsilylchloride, trimethylsilanol, or a mixture thereof. The sulfuric acid reaction is expected to occur between the sulfuric acid and any silylated compound whether, organic or inorganic, or whether the compound is mono-, di-, tri-, or otherwise substituted with silicon elements. Aliphatic and aromatic organic compounds containing silicon are expected to react in reactive distillation as well. Halosubstituted silyl compounds also react with the sulfuric acid to form the sulfuric acid ester that can be separated from the solvent stream. Halosubstituted silyl compounds refers to bromine, chlorine, fluorine, and iodine-substituted aliphatic or aromatic compounds containing at least one silicon substituent.

The solvent waste stream may be optionally pretreated by hydrolysis to remove water-soluble solvents present in the waste stream. The water-soluble silyl compounds, convert to a siloxane during hydrolysis and improves the yield of the recovered silyl compounds. The pretreatment is accomplished by washing the waste stream with an excess of water. The reaction is generally carried out at a temperature from 60° C. to 70° C. Examples of components that are suitable for pretreatment include, but are not limited to, hexamethyldisilazane, trimethylsilane, tetramethylsilane, trimethylsilylchloride, and trimethylsilanol.

Additional optional pretreatment removes chlorine-based and other non-silylated solvent impurities. The additional components, such as benzene, dichloromethane, and acetonitrile, are removed by fractional distillation and other traditional methods of distillation useful in separating components having distinct boiling points. These traditional methods of distillation are described in Kirk-Othner, *Encyclopedia of Chemical Technology*, 4th ed. (1993), pp. 311–358 and Seader & Kurtyka, *Perry's Chemical Engineer Handbook*, 6th. ed. (1984), pp. 13-1 to 13-97, and are incorporated herein by reference.

Preferably, the solvent waste stream feeds continuously into the reactive distillation apparatus to maintain sulfuric acid and solvent reaction. Any means sufficient for maintaining continuous feed into the reaction distillation column can be used. Exemplary means suitable for the continuous process include pumps, feeds, and other devices for transfer or delivery of solvent. Flow rate of the process depends on the scale of operation, feed composition, degree of purity of the reagent, and the like. Exemplary reaction conditions for the reactive distillation include the sulfuric acid solution flow rate of 20 cc/min. In particular for a heptane/hexamethyldisiloxane feed stream, the ratio of 150 cc/min. flow rate of heptane to 30 cc/min. flow rate of sulfuric acid is generally maintained.

Alternatively, delivery of the solvent waste stream occurs in a batchwise manner wherein the solvent feed is treated in specific batch quantities suitable for the process. Quantity of each batch varies and is determined by the capacity of equipment to contain solvent during the reactive distillation.

The temperature of the reaction is maintained at any temperature suitable to keep solvent vapors in a gaseous state during the process of the reaction. The temperature of the solvent vapor at the reboiler is generally in the range from about 20° C. to 100° C., preferably in the range of from about 40° C. to 50° C. Preferably, flash vapor is maintained in the range from about 20° C. to 100° C. at the top of the column. Gaseous solvent vapor reacts with the sulfuric acid solution in the gas-liquid reactive distillation and continues to flows out of the distillation system. Typically, some solvent vapor recondenses during the process of the reaction.

Specific equivalents of the reagents depend on the composition of the feed mixture. Generally, four to five equivalents of heptane feed mixture are treated relative to one equivalent of sulfuric acid.

Any suitable total column height, packed column height, column diameter and number of trays in the extraction distillation column can be employed. The exact dimensions and column designs depend on the scale of the operation, the exact feed composition, the degree of purity of the various products, and the like. The parameters above can be determined by those having ordinary skills in the art.

The invention can be better understood by reference to FIG. 1 and the following description of a preferred embodiment of the invention. The drawing and description are provided for illustrative purposes only and are not meant to limit the disclosure of the invention in any way.

In accordance with FIG. 1, a solvent waste stream is collected at or enters near the bottom of reactive distillation column (1). The feed mixture is heated in reboiler (2) until flash point and flows upward in the distillation column in a gaseous state as a vapor. Downward flowing sulfuric acid enters the column at a point (3) above the vapor. The sulfuric acid contacts the solvent vapor in the column by means of sieve trays (4). The vapor passes through the liquid sulfuric acid to form a silylated sulfuric acid ester which flows downward in the liquid phase until it reaches chimney tray (5). Condensed solvent vapors and the ester are separated in a liquid-liquid separation. Recondensed solvent forms a top layer which can be removed or returned to a flash tank for recirculation. The bottom layer, which is the ester-sulfuric acid portion, is removed to tank (6) and treated by ester hydrolysis. Upward flowing heptane vapors leave the recovery apparatus through the overhead and are condensed for storage and reuse.

Hydrolysis of the silylated sulfuric acid ester solution affords a siloxane compound. The conversion of the ester is accomplished by treating the collection stream with an excess of water. Additional methods of recovering the siloxane from the ester include treating the reaction mixture with an aqueous solution of 5–10% solution of NaOH, $Na_2CO_3$, KOH, and like reagents. The most preferred method of recovering the siloxane is hydrolysis with water.

In another aspect, the invention relates to removing silylated compounds from a gas waste stream. The process of the invention is particularly useful in removing silylated compounds from a gas waste stream comprising the silylated compounds and at least one gas. Preferably, the gas is selected from nitrogen, oxygen, or a mixture thereof.

The gas waste stream is treated with sulfuric acid to convert silylated compounds in the gas waste stream to a silylated sulfuric acid ester. Treatment of the gas waste stream with concentrated sulfuric acid solution affords the ester.

Silylated compounds present in the gas waste stream comprise hexamethyldisilazane, trimethylsilane, tetramethylsilane, trimethylsilylchloride, trimethylsilanol, or a mixture thereof. Sulfuric acid solution reacts with the silylated components of the gas waste stream to form the silylated sulfuric acid ester.

Suitable sulfuric acids useful in the process of the invention are reagent grade sulfuric acid solutions. Preferably, the sulfuric acid is at least 96% grade in purity.

The reaction is accomplished in any vessel suitable for containing a gas-liquid separation and allowing contact between the gas waste stream and liquid sulfuric acid. Preferably, the vessel is a scrubbing column. Any suitable total column height, packed column height, column diameter and column packing can be employed. The exact dimensions and column designs depend on the scale of the operation, the exact feed composition, the degree of purity of the various product and the like. The parameters above can be determined by those having ordinary skills in the art.

Typically, suitable column packing provides surface area for the gas feed mixture to contact the liquid sulfuric acid in a gas-liquid reaction. The diameter of the column will vary in accordance with the amount of gas feed and the rate of gas feed. In the present invention, 3" teflon piping was used for gas feed at a rate of 1.5 cfm.

Entrained sulfuric acid present in the gas stream after reaction is removed by mixing sodium hydroxide solution with the exhausted gas to eliminate trace sulfuric acid. The spent sulfuric acid can then be treated with water to hydrolyze the ester and obtain a siloxane compound. Preferably, the sodium hydroxide solution used is 4 N sodium hydroxide solution.

Silylated compounds can be recovered from the sulfuric acid solution in a similar manner as described in recovering silylated compounds from the silylated sulfuric acid ester separated from the solvent waste stream. Preferably, the silylated compounds are recovered by hydrolyzing the separated ester.

The foregoing may be better understood by reference to the Examples, which are provided for illustrative purposes only and not limitation upon the invention.

Abbreviations used herein and referred to throughout describe the following terms: HMDO for hexamethyldisiloxane; HMDS for hexamethyldisilazane; and TMS for trimethylsilanol.

EXAMPLES

Example 1

Solvent Waste Stream Removal and Recovery of Silylated Compounds

A mixed solution containing 73.1% of heptane isomers, 5.9% HMDO, 1.7% acetonitrile, 4.5% trimethylsilanol (TMS), 0.1% isopropanol and 0.1% cyclohexanone was fed through the bottom port of a continuous liquid-liquid extractor at a rate of 115 cc/min. At the same time, a 3% sulfuric acid solution at a rate of 85 cc/min. and a water solution at a rate of 30 cc/min. were fed through the two ports above the feed port. The washed heptane was collected in a container and the composition at the end of the run was as follows: 89% heptanes, 9% HMDO, 0.1% cyclohexanone and 0.1 TMS.

The above heptane stream was then preheated and fed to the reactive distillation column at a rate of 150 cc/min. directly into the flash tank. At the same time a 96% sulfuric acid solution was fed at a rate of 20 cc/min. through out a port located above the sieve trays section. The upward flowing heptane vapors were continuously condensed and recovered into a container. The recovered heptanes had a purity of 99.9% with a HMDO content of less than 100 ppm. The downward flowing sulfuric acid was contacted with the upward flowing heptane/HMDO vapors by means of six sieves trays in series. The combined liquid stream of the silylated sulfuric acid ester and condensed solvent were collected on a chimney tray for liquid-liquid separation in a continuous manner. The top layer of solvent was allowed to return to the flash evaporator and the more dense sulfuric ester solution was withdrawn out of the apparatus on a continuous basis and collected into a container. The heaviest components of the feed were accumulated on the flash evaporator and intermittently removed.

The collected sulfuric ester was then fed to a liquid-liquid continuous extractor through the feed port at a rate of 100 cc/min. At the same time fresh water was fed through a port above the feed port at a rate of 67 cc/min. The ester was hydrolyzed in a continuous manner and the HMDO produced left the extractor apparatus through the top port. The HMDO recovered had a purity of 95%.

Example 2

Gas Waste Stream Removal of Silylated Compounds

A side stream from the main waste gas header of the chemical plant was allowed to flow through the gas feed port into the scrubber column pilot unit. The pilot unit consisted of a 3" diameter teflon lined pipe packed with stainless steel goodloe packing (572 $ft^2/ft^3$ contact area) which provided efficient gas/liquid contacting and a tank for sulfuric acid recirculation. The waste gas flowed upward through the packing at a rate of 1.5 cfm contacting the downward flowing sulfuric acid. The sulfuric acid, from the recirculation tank entered the column through the upper port at rate of 500 cc/min. and left the scrubber through the bottom outlet and flowed back to the recirculation tank. The treated waste gas leaving the scrubber was allowed to flow and bubbled into a tank containing a 4 normal caustic solution. The gas waste stream leaving this tank was then returned to the main waste gas header.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art, and may be made without departing from the spirit and scope of the invention.

What is claimed is:

1. A method of removing silylated compounds from a solvent waste stream, comprising:

a.) reactively distilling the solvent waste stream with sulfuric acid to form a silylated sulfuric acid ester; and b.) separating the ester from the waste stream.

2. The method according to claim 1, further comprising recovering a silylated compound from the ester of step (b).

3. The method according to claim 1, wherein the solvent waste stream comprises organic solvents, inorganic solvents, aqueous solvents, anhydrous solvents, or any mixture thereof.

4. The method according to claim 3, wherein the solvent waste stream comprises heptane, isomers of heptane, or a mixture thereof.

5. The method according to claim 2, wherein the silylated compound is recovered by hydrolyzing the ester of step (b).

6. The method according to claim 1, wherein the solvent waste stream is pretreated with a hydrolyzing agent.

7. The method according to claim 1, wherein the process is either continuous or batchwise.

8. A method of removing silylated compounds from a gas waste stream, comprising:

a.) treating the gas waste stream with sulfuric acid to form a silylated sulfuric acid ester; and b.) separating the ester from the waste stream.

9. The method according to claim 8, further comprising recovering a silylated compound from the ester of step (b).

10. The method according to claim 9, wherein the silylated compound recovered from the gas waste stream is hexamethyldisilazane, hexamethyldisiloxane, trimethylsilane, tetramethylsilane, trimethylsilanol, trimethylsilylchloride, or a mixture thereof.

11. The method according to claim 8, wherein the gas waste stream comprises nitrogen, oxygen, or a mixture thereof.

12. The method according to claim 8, wherein the gas waste stream is treated with sulfuric acid by a gas-liquid reaction.

* * * * *